(12) United States Patent
Lehner et al.

(10) Patent No.: US 7,193,112 B2
(45) Date of Patent: Mar. 20, 2007

(54) PROCESS FOR THE PRODUCTION OF AROMATIC AMINES BY HETEROGENEOUSLY CATALYSED HYDROGENATION

(75) Inventors: Peter Lehner, Ratingen (DE); Thomas Turek, Düsseldorf (DE); Matthias Brandt, Wuppertal (DE); Susanne Buchholz, Köln (DE)

(73) Assignee: Bayer MaterialScience AG, Leverkusen (DE)

( * ) Notice: Subject to any disclaimer, the term of this patent is extended or adjusted under 35 U.S.C. 154(b) by 232 days.

(21) Appl. No.: 10/960,455

(22) Filed: Oct. 7, 2004

(65) Prior Publication Data

US 2005/0080293 A1  Apr. 14, 2005

(30) Foreign Application Priority Data

Oct. 13, 2003  (DE) ............................... 103 47 439

(51) Int. Cl.
*C07C 209/36* (2006.01)
(52) U.S. Cl. .................. 564/423; 564/415; 564/417; 564/418; 564/420; 564/421; 564/422
(58) Field of Classification Search .................. None
See application file for complete search history.

(56) References Cited

U.S. PATENT DOCUMENTS

| | | | |
|---|---|---|---|
| 3,136,818 A | 6/1964 | Sperber et al. | 260/580 |
| 4,265,834 A | 5/1981 | Birkenstock et al. | 564/421 |
| 5,877,350 A | 3/1999 | Langer et al. | 564/423 |
| 6,005,143 A | 12/1999 | Machado et al. | 564/423 |
| 6,043,394 A | 3/2000 | Langer et al. | 564/423 |
| 6,479,704 B1 | 11/2002 | Nordquist et al. | 564/423 |
| 6,610,628 B2 | 8/2003 | Nordquist et al. | 502/159 |
| 6,730,631 B1 | 5/2004 | Eberle et al. | 502/350 |
| 2003/0004059 A1* | 1/2003 | Haake et al. | 502/301 |
| 2003/0027718 A1 | 2/2003 | Nordquist et al. | 502/159 |
| 2003/0036477 A1 | 2/2003 | Nordquist et al. | 502/527.19 |
| 2003/0157003 A1 | 8/2003 | Machado et al. | 422/242 |

FOREIGN PATENT DOCUMENTS

GB   1 452 466   10/1976

* cited by examiner

*Primary Examiner*—Brian Davis
(74) *Attorney, Agent, or Firm*—Joseph C. Gil; Lyndanne M. Whalen; N. Denise Brown

(57) ABSTRACT

The invention describes a process for the production of aromatic amines by the catalytic hydrogenation of aromatic nitro compounds, with the process being characterized by at least one catalytic hydrogenation step and the catalyst consists at least of a monolithic support and a catalytically active coating.

12 Claims, No Drawings

PROCESS FOR THE PRODUCTION OF AROMATIC AMINES BY HETEROGENEOUSLY CATALYSED HYDROGENATION

BACKGROUND OF THE INVENTION

The invention relates to a process for the production of aromatic amines by the catalytic hydrogenation of aromatic nitro compounds.

Aromatic amines are important intermediates, which have to be produced at low cost and in large quantities. Production plants for aromatic amines are therefore generally constructed for very large capacities. The hydrogenation of nitro-aromatics is a strongly exothermic reaction. The dissipation and energy utilisation of the heat of reaction is therefore an important factor in the production of nitroaromatics.

Various reactors are suitable for the gas phase hydrogenation of nitroaromatics. Thus, for example, in U.S. Pat. No. 3,136,818, a process is described in which the reaction is carried out in a fluidised bed. The effective dissipation of heat in this method is impeded by problems resulting from the non-uniform residence time distribution (break-through of the nitroaromatics) and from catalyst abrasion.

Other processes use stationary catalysts in fixed beds. With this arrangement, the reaction can be performed with a very narrow residence time distribution and avoiding the problem of catalyst abrasion. By operating the fixed bed reactor adiabatically, problems of heat dissipation can be avoided. A process of this type, which is distinguished by a simple construction and easy scalability of the individual pieces of apparatus, is described in, for example, EP-A 0 696 574. To keep the adiabatic temperature increase within limits, however, very large gas streams have to be fed into the circulation in the adiabatic operating method.

In DE-A 28 49 002, a process for the reduction of nitro compounds in the presence of stationary, palladium-containing, multi-component supported catalysts in cooled shell-and-tube reactors is described. The contact consists substantially of 1 to 20 g of palladium, 1 to 20 g of vanadium and 1 to 20 g of lead per litee of $\alpha$-$Al_2O_3$. It has proved advantageous here if the active components are present precipitated as close as possible to the surface of the catalyst in a very sharply defined zone and no active components are contained in the inside of the support material. One disadvantage in the gas phase hydrogenation described in DE-A 28 49 002 is the low specific loading of the catalysts. The loadings quoted are approx 0.4 to 0.5 kg/(l·h). The loading is defined here as the quantity of nitroaromatics in kg per litre of catalyst bed passed through within an hour. Associated with the low catalyst loading is an unsatisfactory space-time yield in industrial-scale processes for the production of aromatic amines. Moreover, the selectivities at the beginning of a run period are distinctly lower than towards the end, which leads to losses of yield and problems in working up the crude product.

The loading of the catalyst can be increased in isothermally operated reactors only if the heat released during the reaction can be efficiently dissipated. In WO 98/25881, the use of inert materials to dilute the catalyst bed in the production of aromatic amines is described. As a result of the dilution, the reaction zone is extended and thus the area available for heat exchange is enlarged. With this method, the hot-spot temperature can be reduced or the possible nitroaromatics loading increased with a constant hot-spot temperature. As a result of the dilution, however, the service life of the bed decreases. In the example quoted in WO 98/25881, the productivity of the diluted bed was markedly lower than the productivity of the undiluted bed because of the short service lives, despite a higher loading.

In another process variation, the hydrogenation of nitroaromatics is performed in thermostatically controlled shell-and-tube reactors. Supported copper or palladium catalysts, among others, are used as catalysts. In GB-A 1 452 466, a process for the production of aniline in a thermostatically controlled shell-and-tube reactor using a supported copper catalyst is described. To complete the conversion, a catalyst bed is used there as an adiabatic secondary reactor.

In DE-A 199 31 902, a process for the production of monolithic oxidation catalysts and their use in the gas phase oxidation of hydrocarbons is described. Here, a monolithic honeycomb catalyst is connected as an adiabatic reactor downstream of the isothermally operated main reactor.

The object of the present invention is to provide a process for the production of aromatic amines by the catalytic hydrogenation of aromatic nitro compounds, which can be carried out on an industrial scale and, compared with the processes known from the prior art carried out in shell-and-tube reactors, makes possible a higher space-time yield and longer service life.

SUMMARY OF THE INVENTION

The present invention provides a process for the production of aromatic amines by the catalytic hydrogenation of aromatic nitro compounds. This process comprises (1) catalytically hydrogenating one or more aromatic nitro compounds in the presence of a catalyst comprising at least of a monolithic support and a catalytically active coating. There is at least one catalytic hydrogenation step in the process of the present invention.

The term monolith, as used in the present invention, is defined, for example, in "Monoliths in multiphase catalytic processes—aspects and prospects" by F. Kapteijn, J. J. Heiszwolf, T. A. Nijhuis and J. A. Moulijn, Cattech 3, 1999, p. 24. According to this reference, monoliths are understood to be not only the "classical" substrates with parallel channels that are not radially inter-connected. They also include foams, sponges and the like which have three-dimensional connections within the substrate to the monoliths as well as substrates with cross-flow channels.

The low-pressure-drop, monolithic support can have a honeycomb structure, but it may also have an open or closed cross-channel structure. The monolithic support possesses a preferred cell density of 100 to 900 cpsi (cells per square inch), and more preferably of 200 to 600 cpsi.

Suitable as materials for the monolithic support are ceramic materials, such as, for example, cordierite, silicates, silicon dioxide, silicon carbide, aluminium oxide, aluminates, mullites or mixtures of these substances, as well as metals and metal alloys.

The monolithic support can be provided with a catalytically active coating using common processes known from the prior art. A process known as dip coating is preferably used for the coating. The dip coating process is described, for example, in "Preparation of monolithic catalysts" by T. A. Nijhuis, A. E. W. Beers, T. Vergunst, I. Hoek, F. Kapteijn and J. A. Moulijn in Catalysis Reviews, volume 43, 2001, pages 345–380. Here, the monolithic support is coated with a suspension based on an extremely finely ground, $Al_2O_3$-supported, catalytically active component.

The catalytically active coating for the hydrogenation of aromatic nitro compounds in the gas phase preferably contains one or more metals from groups VIIIa, Ib, IIb, IVa, Va, VIa, IVb and Vb of the periodic table (Mendeleev) as catalytically active component. Preferred metals include, for example, Pd, Pt, Cu and/or Ni. The catalytically active component can be supported. Suitable materials to be used as the support substance are ceramic substances, such as e.g. $Al_2O_3$, $SiO_2$, $TiO_2$ or zeolites, but also graphite or carbon. The support substance is preferably finely ground. The catalyst described in DE-A 28 49 002, which is believed to correspond to U.S. Pat. No. 4,265,834, the disclosure of which is hereby incorporated by reference, is particularly preferably used as the catalytically active coating.

In order to achieve a uniform coating, the volume-based particle size $d_{90.3}$ of the preferably ground support substance should preferably be less than 50 µm, particularly preferably less than 10 µm.

The particular advantage of the dip-coating process is that a thin layer of a catalytically active component can be applied comparatively easily on to a monolithic support. With the dip-coating process, a catalytically active coating with a film thickness of no more than 250 µm, preferably of no more than 100 µm, and particularly preferably of 10 to 100 µm, can be applied on to the monolithic support. The dip coating can be performed one or more times. By repeated coating, monolithic supports with a catalytically active material, consisting of support substance and catalytically active component, especially up to no more than 150 g/l, preferably of 30 to 150 g/l, and more preferably of 50 to 120 g/l, of monolithic support can be produced.

The process according to the invention is suitable to be carried out on an industrial scale. This process exhibits a higher space-time yield and longer service life compared with the processes known from the prior art, particularly those processes carried out in shell-and-tube reactors.

The catalyst of the present invention for the process of producing aromatic amines, consisting of a monolithic support and a catalytically active coating, displays considerable advantages compared with conventional catalyst beds which are known and described in the prior art. On the one hand, the pressure drop of monolithic supports is substantially lower than that of catalyst beds for a comparable flow-through velocity. Conversely, much higher flow velocities are possible through the monolithic support for the same pressure drop. As a result of the low pressure drop, even at very high flow velocities, the use of monolithic supports is advantageous, for example, for use in downstream reactors or in processes that are distinguished by high volume flows and flow velocities. At the same time, substantially more compact reactors can be built with these catalysts. Another advantage is based on the very thin catalytically active coating. If the catalytically active components are deposited in a very thin layer, the influence of diffusion is much smaller than in the case of full catalysts. In addition, if the main reaction is accompanied by secondary reactions, a higher selectivity can be achieved with these very thin catalytically active coatings. Application in a thin layer can also provide advantages in terms of selectivity for valuable products.

The process according to the invention is preferably operated under pressures of 1 to 30 bar, more preferably of 1 to 20 bar, and most preferably of 1 to 15 bar. The temperature of the educt gas mixture before entering the reactor is preferably 200 to 400° C. and the temperature in the catalyst bed is preferably 200 to 500° C. Hydrogen and aromatic nitro compound(s) are fed into the reactor in a molar ratio of hydrogen to nitro group of preferably 3:1 to 100:1. Suitable compounds to be used as the aromatic nitro compound to be hydrogenated include particularly those of the following formula:

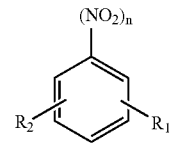

wherein:
R₁ and R₂: may be the same or different and each individually represents a hydrogen atom, or an alkyl group having from 1 to 4 carbon atoms, and preferably a methyl group or an ethyl group, and
n: represents 1 or 2.

Nitrobenzene or the isomers of nitrotoluene are preferably used as the aromatic nitro compounds to be hydrogenated by the process of the invention.

To carry out the process according to the invention, the catalyst can be used, for example, in an adiabatic reactor for the production of aromatic amines as described in, for example, EP-B 0 696 574, believed to correspond to U.S. Pat. No. 5,877,350, the disclosure of which is hereby incorporated by reference. The use of monolithic supports in the process according to the invention is, in principle, also possible in thermostatically controlled reactors. However, the use of such monolithic supports in thermostatically controlled reactors is generally not very advantageous due to the poor radial heat dissipation, particularly on an industrial scale.

According to EP-B 0 696 574, believed to correspond to U.S. Pat. No. 5,877,350, the disclosure of which is hereby incorporated by reference, a ratio of hydrogen:nitro groups of 60:1 to 800:1 is desirable for performing the reaction adiabatically in the hydrogenation of nitroaromatics. Since only 3 equivalents of hydrogen are consumed per nitro group in the hydrogenation, the reaction is conducted with a very large hydrogen excess. This large hydrogen excess results in the gas volume streams in commercial production plants becoming very large. Thus, a small pressure drop in the reactor is an important criterion in the selection of the catalyst. Monolithic supports, including, for example, honeycombs, have a substantial advantage here over a comparable catalyst bed.

The production of aromatic amines can also be carried out by the process according to the invention in a two-step or a multi-step process. In the two-step embodiment of the process, the reaction is carried out first, for example, in an isothermally operated, thermostatically controlled main reactor, with a stationary catalyst bed, wherein the degree of conversion can be 80% to 100%. As mentioned e.g. in DE-A 28 49 002, believed to correspond to U.S. Pat. No. 4,265, 834, the disclosure of which is hereby incorporated by reference, and WO 98/46557, believed to correspond to U.S. Pat. No. 6,080,890, the disclosure of which is hereby incorporated by reference, the hydrogenation of nitroaromatics is accompanied by coking of the catalyst. In reactors with a stationary catalyst bed, this leads to a break-through of the bed. From this point, the nitroaromatics can no longer be 100% converted due to the deactivation of the catalyst bed. The downstream, adiabatically operated secondary reactor is utilised to complete the conversion to 100% when the rate of conversion in the main reactor is less than 100%. By using the adiabatic secondary reactor, the service life of the isothermal main reactor can be increased. Thus, the present invention is particularly advantageous in association with the retrofitting of existing thermostatically controlled shell-and-tube reactors with the goal of increasing the space-time yield.

In another preferred embodiment the process is a two-step process, with an isothermally operated, thermostatically controlled main reactor-with a stationary catalyst bed being used in the first step and an adiabatically operated secondary reactor with a catalyst comprising a monolithic support in the second step. Here, the catalyst bed in the main reactor is diluted with inert material. The dilution of the catalyst bed with inert material enables the catalyst loading to be increased, as described for example in WO 98/46557, believed to correspond to U.S. Pat. No. 6,080,890, the disclosure of which is hereby incorporated by reference. As a diluting material (inert material), for example, the inert catalyst support of the catalyst bed or other inert fillers of glass, ceramic or metal can be used. Substances with high thermal conductivity are preferably used. The catalyst is generally diluted with 10 to 50 vol. % inert material, and preferably with 20 to 40 vol. % inert material. However, as a result of diluting the bed, the service life of the reactor decreases as there is less active catalyst in the reaction volume. This loss of service life can be compensated for by the use of an adiabatically operated secondary reactor. Through the combination of a diluted catalyst bed in a main reactor and an adiabatic secondary reactor, the productivity of the overall process can be increased. This process is especially suitable for existing reactors. By using the monolithic support with a very low pressure drop, the secondary reactor can be integrated into the existing reaction circulation without any problems. With the monolithic support, e.g. honeycomb, it is even possible to achieve flow velocities of more than 10 m/s, for example, in the secondary reactor. This results in the possibility of reducing the residence times in the secondary reactor to values of less than 1 s. Therefore, the selectivity of the main reactor is scarcely affected by secondary reactions in the secondary reactor. Thus, the capacity of existing reactors for the hydrogenation of nitroaromatics can be increased at very low cost by retrofitting an adiabatic secondary reactor with a monolithic catalyst.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all parts and percentages are parts by weight and percentages by weight, respectively.

EXAMPLES

Example 1

Production of Catalytically Coated Monolithic Honeycombs

Cylindrical honeycombs of cordierite with a length of 152 mm, a diameter of 30.5 mm and a cell density of 400 cpsi were used as monolithic supports. The monolithic supports were cleaned, dried and weighed before coating. The composition of the supported, catalytically active components used as the catalytically active coating was as follows: 9 g palladium, 9 g vanadium and 3 g lead per liter of spherical alpha-aluminium oxide. (A detailed description of the supported catalyst can be found in DE-A 28 49 002, believed to correspond to U.S. Pat. No. 4,265,834, the disclosure of which is hereby incorporated by reference.) From these supported, catalytically active components, a powder with a particle size of $d_{50.3}=1.7$ µm and $d_{90.3}=4.9$ µm was produced by comminution and extremely fine grinding prior to coating.

For the coating suspension, a solution of 3.2 g of 25 wt. % aqueous ammonium polymethacrylate solution ("Darvan C" from R. T. Vanderbilt) and 116.8 g of deionised water was prepared, into which 80.0 g of the extremely finely ground catalyst were then incorporated. The solids content of the suspension was thus approx. 40 wt. %. A honeycomb was then immersed in this suspension for several minutes. After it was removed from the suspension, the honeycomb was left to drain and then the channels were blown clear with a compressed air gun. Drying (2 h at 120° C. in a circulating air drier) and calcination (2 h at 500° C. in a muffle furnace) then took place. The coated honeycomb was then weighed again.

The loading of the monolithic support with the catalytically active material, consisting of support substance and catalytically active component, was 68 g/l and the film thickness of the catalytically active coating was no more than 100 µm.

A total of seven honeycombs were coated with catalyst in the manner as described above. The catalyst loadings achieved, as represented by $w_K$, and calculated according to the formula:

$$w_K = \frac{mass_{honeycomb\ after\ coating} - mass_{honeycomb\ before\ coating}}{mass_{honeycomb\ after\ coating}}$$

were from 10 to 14 wt. %.

Example 2

Standard Bed (Comparative Example)

A tubular reactor thermostatically controlled with oil, having an internal diameter of 26 mm and a length of 3000 mm, was filled with a catalyst as described in DE-A 28 49 002 which is believed to correspond to U.S. Pat. No. 4,265,834, the disclosure of which is hereby incorporated by reference. A protective tube with a mobile thermocouple was located in the center of the tubular reactor to detect the temperature in the catalyst bed. The catalyst was flushed first with nitrogen and then with hydrogen, and was then activated with 1,000 l/h hydrogen at 240° C. over a period of 49 h.

Nitrobenzene was then evaporated in a mixture of nitrogen and hydrogen. The nitrobenzene loading was slowly increased from 134 g/h to the maximum value of 690 g/h in such a way that the maximum temperature in the bed did not rise above 460° C. In this phase, an 820 l/h volume flow of the mixture was passed through the reaction tube, maintaining a 4 to 1 molar ratio of hydrogen to nitrobenzene. When the maximum quantity of nitrobenzene was reached, the nitrogen was completely replaced by hydrogen and 820 l/h of hydrogen were then passed through the reaction tube. The oil temperature was kept at a constant 240° C. throughout the reaction period.

In the area of the maximum nitrobenzene loading, the hot spot migrated through the bed at a rate of approx. 1 mm/h.

At the maximum nitrobenzene loading, the maximum temperature was 435° C. The selectivity was 98.7% after 47 h, 99.5% after 119 h and 99.5% after 408 h.

Example 3

Use of the Monolithic Honeycomb (Example of an Embodiment)

Monolithic honeycombs produced according to Example 1 were used as catalysts in a tubular reactor thermostatically controlled with oil, having an internal diameter of 32.8 mm. Five (5) honeycombs, each with a length of 150 mm and a diameter of 30.5 mm, were introduced into the reaction tube. The active catalyst material deposited on these 5 honeycombs i.e. support substance and catalytically active component, totalled 37.5 g. The gap between the tube wall and the honeycomb was sealed with a heat-resistant fleece (Carborundum, type FT 1). A protective tube with a mobile thermocouple was located in the center of the tubular reactor to detect the temperature in the monolithic honeycomb. The catalyst was flushed first with nitrogen and then with hydrogen, and was finally activated with 500 l/h hydrogen at 300° C. over a period of 3 h.

Nitrobenzene was then evaporated in a mixture of nitrogen and hydrogen. The nitrobenzene loading was increased stepwise from 30 g/h to 110 g/h within 72 h. When a quantity of nitrobenzene of 110 g/h was reached, the nitrogen was completely replaced by hydrogen. 140 l/h of hydrogen were then passed through the reaction tube. The oil temperature was kept at a constant 240° C. throughout the reaction period. The selectivity was more than 99.9% after only 28 h in this case. Thus, compared with the bed (cf. Example 2), distinctly higher selectivities can be achieved with the monolithic honeycomb. Moreover, this high selectivity is achieved more rapidly.

Example 4

Use of the Monolithic Catalyst to Complete Conversion (Mixtures of Aniline, Water and Nitrobeniene)

Monolithic honeycombs produced according to Example 1 were used as catalysts in a tubular reactor thermostatically controlled with oil, having an internal diameter of 32.8 mm. Five (5) honeycombs, each with a length of 150 mm and a diameter of 30.5 mm, were introduced into the reaction tube. The active catalyst material deposited on these 5 honeycombs, i.e. support substance and catalytically active component, totalled 37.5 g. The gap between the tube wall and the honeycomb was sealed with a heat-resistant fleece (Carborundum, type FT 1). A protective tube with a mobile thermocouple was located in the center of the tubular reactor to detect the temperature in the monolithic honeycomb. The catalyst was flushed first with nitrogen and then with hydrogen, and was finally activated with 700 l/h hydrogen at 300° C. over a period of 24 h.

Aniline and water in a molar ratio of 1 to 2 were then evaporated in a hydrogen stream. Nitrobenzene was added to the water, the proportion of nitrobenzene being varied according to the aniline used. The quantities of aniline, water, nitrobenzene and hydrogen throughput were varied within a broad operating window (cf. Table 1). The oil temperature was kept at a constant 300° C. throughout the reaction period. In all cases, the nitrobenzene used could be converted almost completely with the monolithic honeycombs used.

TABLE 1

Parameters of the tests carried out in the bed

| | Case 1 | Case 2 | Case 3 | Case 4 |
|---|---|---|---|---|
| Aniline | 612 g/h | 612 g/h | 612 g/h | 1448 g/h |
| Nitrobenzene | 0.1 g/h | 0.6 g/h | 66.6 g/h | 257 g/h |
| Hydrogen | 450 l/h | 450 l/h | 1685 l/h | 1685 l/h |
| Nitrobenzene in educt | 19 ppm | 998 ppm | 9.8 wt. % | 15 wt. % |
| Nitrobenzene in product | 5 ppm | 3 ppm | 1 ppm | 3 ppm |

Example 5

Diluted Bed (Example of an Embodiment)

A mixture of 50 vol. % of the catalyst described in DE-A 28 49 002, which is believed to correspond to U.S. Pat. No. 4,265,834, the disclosure of which is hereby incorporated by reference, and 50 vol. % SiC (SIKA I F8 from Norton SIKA) was introduced into the tubular reactor described in Example 2 to dilute the catalyst bed. The bed was activated with hydrogen as described in Example 2.

a) The nitrobenzene loading was then increased stepwise to a maximum quantity of 723 g/h, as described in Example 2. From the point when the maximum quantity of nitrobenzene was reached, 852 l/h of hydrogen were passed through the bed. The selectivity was 98.0% after 52 h, 98.5% after 121 h and 99.5% after 409 h.

b) In the same way as in a), with the same bed, a maximum quantity of nitrobenzene of 1,236 g/h and 1,460 l/h of hydrogen were used. The selectivity was 92.2% after 48 h, 98.3% after 123 h and 99.7% after 408 h.

c) In the same way as in a), with the same bed, a maximum quantity of nitrobenzene of 2,028 g/h and 2211 l/h of hydrogen were used. The selectivity was 98.4% after 50 h, 99.4% after 124 h and 99.7% after 220 h.

In all cases, lower temperatures were measured in the area of the hot spot compared with the undiluted bed (see Example 2). Due to the higher specific catalyst loading, however, the hot spot migrates through the bed more rapidly in all these examples than is the case in Example 2(see Table 2).

TABLE 2

Parameters of the tests carried out in the bed

| | Example 2 | Example 5a | Example 5b | Example 5c |
|---|---|---|---|---|
| Nitrobenzene | 690 g/h | 732 g/h | 1236 g/h | 2028 g/h |
| Hydrogen | 820 l/h | 852 l/h | 1460 l/h | 2211 l/h |
| Rate of migration | 1 mm/h | 1.7 mm/h | 2.3 mm/h | 4.4 mm/h |
| $T_{hot\ spot,\ max}$ | 435° C. | 332° C. | 370° C. | 401° C. |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of aromatic amines comprising
   (1) catalytically hydrogenating one or more aromatic nitro compounds in the presence of a catalyst comprising a monolithic support and a catalytically active coating;
   wherein the temperature of the educt gas mixture ranges between 200° C. and 400° C. prior to entering the reactor and the hydrogenation occurs in an adiabatically operated reactor at a temperature of from 200° C. to 500° C.

2. The process of claim 1, wherein the cell density of the monolithic support is from 100 to 900 cpsi.

3. The process of claim 2, wherein the cell density of the monolithic support is from 200 to 600 cpsi.

4. The process of claim 1, wherein the catalytically active coating has a film thickness of no more than 250 μm.

5. The process of claim 4, wherein the catalytically active coating has a film thickness of no more than 100 μm.

6. The process of claim 4, wherein the catalytically active coating has a film thickness of 10 to 100 μm.

7. The process of claim 1, wherein the catalytically active coating comprises platinum and/or palladium.

8. The process of claim 1, wherein the catalytically active coating contains supported platinum and/or palladium.

9. The process of claim 1, wherein the catalytic hydrogenation takes place under a pressure of 1 to 30 bar.

10. The process of claim 9, wherein the catalytic hydrogenation takes place under a pressure of 1 to 20 bar.

11. The process of claim 9, wherein the catalytic hydrogenation takes place under a pressure of 1 to 15 bar.

12. The process of claim 1, in which the catalytic hydrogenation is carried out in two steps, wherein the second catalytic hydrogenation step occurs in an adiabatically operated reactor with a catalyst comprising at least a monolithic support and a catalytically active coating.

* * * * *